United States Patent [19]

Antoshkiw et al.

[11] 4,316,917
[45] Feb. 23, 1982

[54] STABLE CAROTENOID SOLUTIONS

[75] Inventors: Thomas Antoshkiw, Kearny; Marco A. Cannalonga, Fort Lee; Frank Guerin, Bloomfield, all of N.J.

[73] Assignee: Hoffman-La Roche Inc., Nutley, N.J.

[21] Appl. No.: 142,273

[22] Filed: Apr. 21, 1980

[51] Int. Cl.³ .............................................. A23L 1/27
[52] U.S. Cl. ...................................... 426/540; 426/73
[58] Field of Search ................. 426/540, 250, 73, 654, 426/268, 807; 252/363.5

[56] References Cited

U.S. PATENT DOCUMENTS

| | | | |
|---|---|---|---|
| 3,039,877 | 6/1902 | Borenstein | 426/540 X |
| 3,158,487 | 11/1964 | Reid | 426/654 X |
| 3,206,316 | 9/1965 | Klaui | 426/540 |
| 3,227,561 | 1/1966 | Mima | 426/202 X |
| 3,499,917 | 3/1970 | Brandner | 426/654 X |
| 3,734,745 | 5/1973 | Cassanelli | 426/540 X |
| 3,886,294 | 5/1975 | Emodi | 426/250 X |

FOREIGN PATENT DOCUMENTS

| | | | |
|---|---|---|---|
| 208084 | 4/1960 | Austria | 426/250 |
| 1168232 | 4/1964 | Fed. Rep. of Germany | 426/540 |

*Primary Examiner*—Robert Halper
*Attorney, Agent, or Firm*—Jon S. Saxe; George M. Gould; William H. Epstein

[57] ABSTRACT

Stable carotenoid solutions useful as colorants in foods and which are dispersible in water or soluble in oil-based products or emulsions are disclosed.

8 Claims, No Drawings

STABLE CAROTENOID SOLUTIONS

BACKGROUND OF THE INVENTION

Carotenoids such as carotene, lycopene, bixin, zeazantin, cryptoxanthin, lutein, canthaxanthin, β-apo-8'-carotenal, β-apo-12'-carotenal and esters of hydroxy- or carboxy-containing members of this group have attained considerable importance as coloring agents. This importance has increased due to possible governmental regulations withdrawing or limiting the use of certain previously certified coloring agents.

Carotenoids are yellow to red pigments either identical with or related to pigments occurring in the plant and animal kingdom. Because of this relationship to naturally occurring pigments, carotenoids possess considerable interest as replacements for the synthetic coloring agents for use as coloring materials, e.g., for foodstuffs and pharmaceutical or cosmetic properties. In addition, the carotenoids are used in animal feedstuffs to provide, for example, enhanced egg yolk or skin pigmentation as well as a source of vitamin A activity.

Carotenoids are substances which are insoluble in water and which have relatively high melting points. Moreover, carotenoids are substances which are very sensitive to oxidation. These characteristics militate against direct employment of the crystalline materials for coloration of aqueous foodstuffs or feedstuffs of for use as a source of vitamin A since, in this form, the materials are poorly absorbed or give poor coloring effects. The above-mentioned characteristics of carotenoids are especially disadvantageous in the coloring of aqueous media since, as a result of the water-insolubility of carotenoids, it is quite difficult to obtain a homogeneous or sufficiently intense color effect. Hence, the water insolubility of the carotenoids prevents their direct use as coloring agents for coloring foodstuffs having an aqueous base such as fruit juices, mineral water with fruit juices or with fruit juice flavors, ice-cream, etc. and dry products which are to be added to water in their original form or first prepared with water prior to use such as, for example, pudding powders, soup powders, powdered eggs, tomato concentrates and dry beverage bases such as lemonade powder.

SUMMARY OF THE INVENTION

This invention relates to stable carotenoid solutions which can be dispersed in aqueous systems or solubilized in either oil-based media or in emulsions. The dual application of these solutions, i.e. their use in oil-based or water-based products, is a distinct advantage for carotenoid solutions. Thus, these stable carotenoid solutions can be used as coloring agents, e.g. for foodstuffs, salad dressings, beverages, dairy products and the like. The stable carotenoid solutions contain, in addition to the carotenoid, a surfactant, glycerol monocaprylate and propylene glycol dicaprylate-dicaprate as solubilizers and an antioxidant.

DETAILED DESCRIPTION OF THE INVENTION

Carotenoids are the known natural or synthetic available representatives of this class of compounds useful as coloring agents, e.g. carotene, lycopene, bixin, zeaxantin, cryptoxanthin, lutein, canthaxanthin, β-apo-8'-carotenal, β-apo-12'-carotenal, β-apo-8'-carotenoic acid, and esters of hydroxy- or carboxy-containing members of this group, such as lower alkyl esters and, preferably, methyl and ethyl esters. These carotenoids can be employed singly or in admixtures, depending on the color desired.

Especially preferred as a stable carotenoid solution of this invention is β-apo-8'-carotenal which forms a clear, red-colored oleaginous solution.

Nonionic surfactants are preferred for imparting water-dispersibility to the resulting composition. Especially preferred as the nonionic surfactant is a product comprising a mixture of oleate esters of sorbitol anhydrides, consisting predominantly of the monoester, condensed with approximately 20 moles of ethylene oxide. The mixture has the general formula:

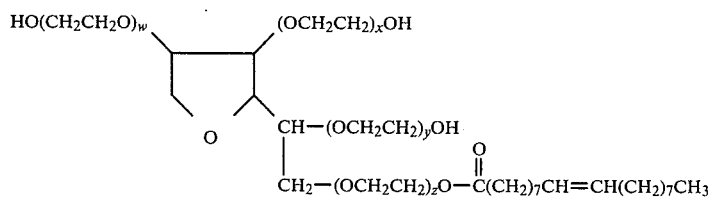

where $w+x+y+z$ has an average value of 20. Commercial examples of such a product include Polysorbate 80 and Tween 80 (ICI United States). Other suitable nonionic surfactants include Tween 60, a polyoxyethylene derivative of sorbitan monostearate, Emulphor EL-620 and Emulphor EL-719, polyoxyethylated vegetable oils (GAF Corp.).

The concentration of the surfactant is critical in the sense that a sufficient amount must be present to impart maximum water dispersibility to the carotenoid solution. A concentration of surfactant ranging from about 25% to about 35% by weight, based on the total weight of the carotenoid solution, is preferred with a concentration of about 30% by weight especially preferred.

As the solubilizer component for the carotenoid in the carotenoid solutions, a combination of two solubilizers has been found especially efficacious. These solubilizers are:

(a) glycerol monocaprylate (GMC-8, PVO International, Inc.), and
(b) Propylene glycol dicaprylate-dicaprate (Mazol PG-810, Mazer Chemicals, Inc.; Neobee M-20, PVO International, Inc.).

Propylene glycol dicaprylate-dicaprate is a mixture of the propylene glycol diesters of caprylic and capric acids.

Formulations were prepared containing a constant amount of surfactant and varying ratio of glycerol monocaprylate and propylene glycol dicaprylate-dicaprate. A ratio of one part of glycerol monocaprylate with from about 1.5 to about 3.5 parts of the dicaprylate-dicaprate is effective for solubilization of the carotenoid in solution. Optimal solubilization is achieved at the ratio of one part of glycerol monocaprylate to about 2.5 parts of the dicaprylate-dicaprate.

Concentration of the solubilizer component in the carotenoid solution can range from about 60% to about 70% by weight with a concentration of about 65% by weight preferred.

As the antioxidant for the carotenoid component of the solution composition, about 1% by weight of dl-α-tocopherol is preferred. The addition of equal quantities of butylated hydroxyanisol (BHA) or butylated hydroxytoluene (BHT) with or without the dl-α-tocopherol had similar antioxidant results.

The concentration of the β-apo-8'-carotenal in the final solution composition is limited, at the lower concentrations, by the necessity for achieving a color intensity sufficient to impart the desired color upon dilution into the various foodstuffs, salad dressings, beverages, dairy products end the like and, at the higher concentrations, by the need to achieve a physically stable solution, e.g., to avoid crystallization of the carotenoid component. A concentration of 2% by weight of β-apo-8'-carotenal is optimal. Higher concentrations, i.e. 3% of carotenal, have a deleterious effect on the physical stability of the solution even at refrigeration temperatures.

The carotenoid solutions of this invention are stable at room temperature and at 45° C. No crystal formation occurred after prolonged refrigeration storage of the solution with alternate periods of warming to room temperature.

The 2% β-apo-8'-carotenal solution of this invention is a clear red-colored oleaginous solution which was developed for use as a colorant for foods, salad dressings, aqueous-based beverages and dairy products. It is, thus, unique in that it can be used in dispersions in water or in solution in oleaginous-based products. Maximum water dispersibility is achieved as a result of the amount of surfactant used.

The desired coloring effect for the various materials is achieved by merely admixing therewith the required amount of the carotenal solution.

The following Examples illustrate the invention:

EXAMPLE 1

2% β-apo-8'-Carotenal Solution

By the procedure described below, a carotenal solution having the following composition is prepared:

| Ingredient | Gm per gm of solution |
| --- | --- |
| β-apo-8'-carotenal | 0.025 |
| Polysorbate 80-K | 0.300 |
| GMC-8 | 0.185 |
| Mazol PG-810 | 0.480 |
| dl-α-tocopherol | 0.010 |

For a 100 kg. batch, 30 kg. of Polysorbate 80-K, 1.0 kg. of dl-α-tocopherol, 18.5 kg. of GMC-8 and 48.0 kg. of Mazol PG-810 are changed to a reaction kettle. This solvent/antioxidant mixture is heated, under nitrogen and with stirring, to 130° C.

2.5 kg. of β-apo-8'-carotenal are added slowly to this solution. Heating of the resulting slurry is continued until solution of the carotenal is complete, i.e. about 2–5 minutes.

Stirring is continued while the solution is gradually cooled, under a nitrogen atmosphere, to 40° C. to a clear, deep-red liquid. The cool solution is then examined microscopically for the presence of any crystals of β-apo-8'-carotenal.

If crystals are present, the solution is reheated to 130° C. to complete the solubilization of the apo-carotenal.

EXAMPLE 2

This Example illustrates the stability of β-apo-8'-carotenal in solutions prepared as described in Example 1.

The following solutions were prepared.

| Ingredient | Formulation (grams/1000 grams) | | | | | | | | |
| --- | --- | --- | --- | --- | --- | --- | --- | --- | --- |
|  | A | B | C | D | E | F | G | H | I |
| β-apo-8'-carotenal | 20 | 22.5 | 22.5 | 22 | 22 | 20 | 25 | 25 | 25 |
| Tween 80 | 300 | 300 | 300 | 300 | 300 | 300 | — | — | — |
| Tween 60 | — | — | — | — | — | — | 300 | — | — |
| Emulphor El-620 | — | — | — | — | — | — | — | 300 | — |
| Emulphor EL-719 | — | — | — | — | — | — | — | — | 300 |
| Mazol PG-810 | 480 | 480 | 480 | 480 | 480 | 480 | 480 | 480 | 480 |
| GMC-8 | 180 | 180 | 180 | 180 | 180 | 180 | 185 | 185 | 185 |
| dl-α-tocopherol | 10 | 10 | 10 | 10 | 10 | 20 | 10 | 10 | 10 |
| BHT | 10 | 10 | 10 | — | — | — | — | — | — |
| BHA | — | — | — | 10 | — | — | — | — | — |

Each formulation was initially assayed for β-apo-8'-carotenal content. Results are reported below:

| Formulation | % β-apo-8'-carotenal |
| --- | --- |
| A | 1.80 |
| B | 2.13 |
| C | 2.19 |
| D | 2.05 |
| E | 2.15 |
| F | 2.06 |
| G | 2.39 |
| H | 2.41 |
| I | 2.46 |

Aliquots of each formulation were stored at room temperature and at 45° C. for periods ranging from 4 weeks to 12 months. After the storage periods, the formulations were again assayed for β-apo-8'-carotenal. Results are tabulated below.

| Storage | | % Carotenal Retention | | | | | | | | |
| --- | --- | --- | --- | --- | --- | --- | --- | --- | --- | --- |
| Temperature | Time | A | B | C | D | E | F | G | H | I |
| 45° C. | 4 weeks | 98 | 100 | 97 | 100 | 100 | 89 | 93 | 93 | 97 |
| 45°0 C. | 8 weeks | 96 | 100 | 97 | 100 | 100 | 89 | 97 | 93 | 100 |

-continued

| Storage | | % Carotenal Retention | | | | | | | | |
|---|---|---|---|---|---|---|---|---|---|---|
| Temperature | Time | A | B | C | D | E | F | G | H | I |
| 45° C. | 16 weeks | 93 | 99 | 95 | 100 | 93 | 85 | 93 | 90 | 94 |
| R.T. | 3 months | 100 | 94 | 95 | 99 | 99 | 93 | 95 | 93 | 93 |
| R.T. | 6 months | 96 | 89 | 100 | 100 | 94 | 86 | 92 | 91 | 91 |
| R.T. | 12 months | 92 | 83 | 90 | 94 | 84 | 92 | 90 | 88 | 79 |

We claim:

1. A stabilized carotenoid composition comprising β-apo-8'-carotenal, a surfactant, a solubilizer component consisting of glycerol monocaprylate and propylene glycol dicaprylate-dicaprate and an antioxidant.

2. The stabilized carotenoid composition of claim 1 comprising, in percents by weight based on the total weight of the composition, about 2% β-apo-8'-carotenal, from about 25% to about 35% of a nonionic surfactant, from about 60% to about 70% of the solubilizer component and about 1% of an antioxidant.

3. The stabilized carotenoid composition of claim 1 comprising about 2% of β-apo-8'-carotenal, about 30% of the nonionic surfactant, about 65% of the solubilizer component and about 1% of dl-α-tocopherol antioxidant.

4. The stabilized carotenoid of claim 3 wherein the surfactant is a mixture of oleate esters of sorbitol anhydrides, consisting predominantly of the monoester, condensed with approximately 20 moles of ethylene oxide.

5. The stabilized carotenoid composition of claim 3 wherein the surfactant is a polyoxyethylene derivative of sorbitan monostearate.

6. The stabilized carotenoid composition of claim 5 wherein the ratio of glycerol monocaprylate to propylene glycol dicaprylate-dicaprate is 1 part to about 2.5 parts.

7. The stabilized carotenoid composition of claim 3 wherein the surfactant is a polyoxyethylated vegetable oil.

8. The stabilized carotenoid composition of claim 3 wherein the solubilizer component comprises one part of glycerol monocaprylate to from 1.5 to about 3.5 parts of propylene glycol dicaprylate-dicaprate.

* * * * *